United States Patent
Laurence et al.

(10) Patent No.: US 7,262,416 B2
(45) Date of Patent: Aug. 28, 2007

(54) GAMMA CAMERA WITH DYNAMIC THRESHOLD

(75) Inventors: Thomas L. Laurence, Parma, OH (US); Steven E. Cooke, Garfield Heights, OH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 183 days.

(21) Appl. No.: 10/536,061

(22) PCT Filed: Nov. 12, 2003

(86) PCT No.: PCT/IB03/05123

§ 371 (c)(1),
(2), (4) Date: May 24, 2005

(87) PCT Pub. No.: WO2004/049001

PCT Pub. Date: Jun. 10, 2004

(65) Prior Publication Data

US 2006/0163486 A1    Jul. 27, 2006

Related U.S. Application Data

(60) Provisional application No. 60/429,504, filed on Nov. 27, 2002.

(51) Int. Cl.
*G01T 1/208* (2006.01)
*G01T 1/161* (2006.01)
*G01T 1/164* (2006.01)
*G01T 1/166* (2006.01)

(52) U.S. Cl. ............ 250/369; 250/363.07; 250/363.04; 250/363.03

(58) Field of Classification Search ................ 250/369, 250/366, 363.04, 363.03, 363.02, 363.07
See application file for complete search history.

(56) References Cited

U.S. PATENT DOCUMENTS 4,074,135 A * 2/1978 Stevens ...................... 250/366

(Continued)

FOREIGN PATENT DOCUMENTS

EP    450388 A2 * 10/1991

(Continued)

OTHER PUBLICATIONS

Geagan, M.J., et al.; Correction of distortions in a discontinuous image; Nuc. Inst. & Meth. in Phys. Res.; 1994; A 353:379-383.

*Primary Examiner*—David Porta
*Assistant Examiner*—Frederick F Rosenberger

(57) ABSTRACT

A method of locating an event with a gamma camera (12) of an emission computed tomography (ECT) scanner (10) is provided. The gamma camera (12) includes a matrix of sensors (22) situated to view the event. The sensors (22) have respective outputs that are responsive to the event. The method includes: identifying a first sensor in the matrix that has in response to the event a highest output relative to the other sensors in the matrix (step (B2)); identifying a number of second sensors in the matrix that are closest neighbors to the first sensor (step (B3)); combining into a total output a number of outputs from the identified sensors, the number of outputs being at least one (1) and less than the number of all the identified sensors (step (B4)); and, determining a threshold value which is a percentage of the total output (step (B4)).

19 Claims, 11 Drawing Sheets

U.S. PATENT DOCUMENTS

| | | | |
|---|---|---|---|
| 4,475,042 A | 10/1984 | Arseneau | 250/363 |
| 5,504,334 A | 4/1996 | Jansen et al. | 250/369 |
| 5,508,524 A | 4/1996 | Goldberg et al. | 250/369 |
| 5,576,547 A | 11/1996 | Ferreira et al. | 250/369 |
| 5,838,010 A | 11/1998 | Pedersen | 250/369 |
| 5,900,636 A | 5/1999 | Nellemann et al. | 250/363.04 |
| 6,169,285 B1 | 1/2001 | Petrillo et al. | 250/369 |
| 6,326,624 B1 | 12/2001 | Chapuis et al. | 250/369 |
| 6,348,692 B1 | 2/2002 | Chapuis et al. | 250/369 |
| 6,376,841 B1 | 4/2002 | Petrillo et al. | 250/363.03 |
| 6,603,125 B1 * | 8/2003 | Cooke et al. | 250/369 |
| 6,723,993 B2 * | 4/2004 | Cooke et al. | 250/369 |
| 2003/0034455 A1 * | 2/2003 | Schreiner et al. | 250/366 |

FOREIGN PATENT DOCUMENTS

| | | |
|---|---|---|
| GB | 1 531 848 | 7/1976 |

\* cited by examiner

PRIOR ART

PRIOR ART

GAMMA CAMERA WITH DYNAMIC THRESHOLD

CROSS REFERENCE TO RELATED APPLICATIONS

This application claims the benefit of U.S. provisional application Ser. No. 60/429,504 filed Nov. 27, 2002, which is incorporated herein by reference.

The present invention relates to the art of nuclear medical imaging. It finds particular application in conjunction with gamma cameras, and will be described with particular reference thereto. It is usable in connection with emission computed tomography ("ECT"), including positron emission tomography ("PET") and single photon emission computed tomography ("SPECT"); whole body nuclear scans; transmission imaging; etc. Those skilled in the art will appreciate that the present invention is also amenable to other like applications and diagnostic imaging modes.

Diagnostic nuclear imaging or ECT is directed to a qualitative and quantitative examination of a distribution of radiotracers, typically, injection into the subject of the examination, e.g., a patient. ECT scanners usually have one or more radiation detectors or gamma cameras that are mounted on a movable gantry to view an examination region which receives the subject therein. Typically, for example, one or more radionuclides or radiopharmaceuticals that generate detectable radiation are introduced into the subject. The radiopharmaceuticals preferably travel to an organ or organs of interest whose image is to be produced. The detectors scan the subject along a selected path or scanning trajectory and radiation events are detected on each gamma camera.

In a traditional scintillation detector, the detector has a scintillator made up of a large scintillation crystal or matrix of smaller scintillation crystals. In either case, the scintillator is viewed by a matrix of sensors. A commonly employed sensor is a photomultiplier tube ("PMT"). A collimator which includes a grid- or honeycomb-like array of radiation absorbent material may be located between the scintillator and the subject being examined to limit the angle of acceptance of radiation which impinges on the scintillator. The relative outputs of the PMTs are processed and corrected to generate a signal indicative of the position and energy of detected radiation events. The radiation data is then reconstructed into an image representation of a region of interest.

Each radiation event impinging on the scintillator generates a corresponding flash of light (scintillation) that is seen by the PMTs. An individual PMT's proximity to the flash's origin affects the degree to which the light is seen by that PMT. Each PMT that sees an event generates a corresponding electrical pulse. The respective amplitudes of the electrical pulses are generally proportional to the distance of each PMT from the flash. Based on the outputs from the PMTs, the gamma camera maps radiation events, i.e., it determines the energy and position of radiation rays impinging the scintillator.

A conventional method for event positioning is known as the Anger method, which sums and weights signals output by PMTs after the occurrence of an event. The Anger method for event positioning is based on a simple first moment calculation. More specifically, the energy is typically measured as the sum of all the PMT signals, and the position is typically measured as the "center of mass" or centroid of all the PMT signals.

Several methods have been used for implementing the centroid calculation. With fully analog cameras, all such calculations (e.g., summing, weighting, dividing) are done using analog circuits. With hybrid analog/digital cameras, the summing and weighting are done using analog circuits, but the summed values are digitized and the final calculation of position is done digitally. With "fully digital" cameras, the PMT output signals will be digitized individually. Regardless of the aforementioned camera type employed, the quality and/or accuracy of the images ultimately reconstructed is dependant on accurately measuring or otherwise determining the location or position of an event so as to match the actual event location or position.

Generally, a scintillation light flash is mostly contained within a small subset of the PMTs. For example, out of a total number of PMTs, typically on the order of 50 or 60, over 90% of a total signal is often detected in the seven (7) PMTs closest to a scintillation flash. However, light from the scintillator undesirably straying to more remote PMTs, noise in the PMT outputs, and the like can effect the centroid calculation in the traditional Anger method because all the PMT outputs are used in the positioning calculation. Accordingly, this may give rise to an artificial shifting of event location measurements. Stray signals also tend to arise at high-counting rates due to events occurring nearly simultaneously in the scintillator. When two events occur substantially simultaneously, their "center-of-mass" is midway between the two—where no event actually occurred. Again, events can be mis-positioned as a result.

The stray or otherwise undesirable signals (i.e., those not bearing a readily ascertainable relationship to an actual event and/or its true location) are typically characterized by lower PMT signal amplitudes as compared to PMT signals associated with and/or corresponding to actual observed events. Using this distinction, techniques have been developed to address the mis-positioning problem associated with stray signals. In particular ways, these techniques aim to selectively limit the number of PMTs used in the centroid calculation and/or limited the contribution thereto from selected PMTs.

One option is to set an arbitrary threshold, and omit from the centroid calculation for an event PMT outputs with amplitudes that due not meet the threshold. Alternately, rather than omitting PMT outputs, the PMT output amplitudes may be reduced by the threshold amount thereby effectively eliminating any contributions from PMT outputs below the threshold. This technique, however, is undesirably inflexible and can at times eliminate or omit PMT outputs that would otherwise be wanted in the centroid calculation or still include PMT outputs that would otherwise not be wanted in the centroid calculation (e.g., from PMTs that are significantly remote from the event).

Another approach involves selecting, for each event, the PMT with the highest output amplitude and a number (usually six (6)) of its closest neighbors. The outputs from only these seven PMTs (known as a 7-PMT cluster) is then use to calculate the centroid for that event. When the PMT are arranged in what is known as close hexagonal packing, the 7-PMT cluster includes a center PMT (i.e., the one with the highest output amplitude) and six (6) surrounding PMTs. Excluding the outlying PMTs also excludes the remote noise therefrom. FIG. 8 is an exemplary illustration of event data generated using the 7-PMT cluster technique. The hexagonal artifact clearly evident is an indication of event mis-positioning.

FIG. 9 is an exemplary illustration of event data generated using a combined thresholding and 7-PMT cluster technique. With this combined technique, the 7-PMT cluster is selected in the same way, however, a threshold is set, and for each event, those PMT outputs with amplitudes less than the threshold are omitted from the centroid calculation for that event. Again, rather than omitting PMT outputs, the PMT output amplitudes may be reduced by the threshold amount thereby effectively eliminating any contributions from PMT outputs below the threshold. The PMT output amplitudes from all the PMTs are summed up or otherwise totaled together, and the threshold is set as a percentage (e.g., 3%) of this total. While improved as compared to FIG. 8, the hexagonal artifact indicative of event mis-positioning is still evident in FIG. 9.

In the aforementioned combined technique or approach, when an event occurs substantially under or well within the boundaries of one of the PMTs, that PMT and the six surrounding PMTs contribute suitably to the centroid calculation and the positioning works relatively well. The difficulty arises when an event occurs at or near a double point (i.e., that region in the vicinity of where two (2) PMTs meet or converge) or a triple point (i.e., that region in the vicinity of where three (3) PMTs meet or converge). See, e.g., FIG. 11 which shows a close hexagonal packed 7-PMT cluster 300 including a center PMT 310 and six (6) surrounding PMTs 312a-312f, an exemplary double point being indicated generally by point 320 and an exemplary triple point being indicated generally by point 322. When the event occurs at the double point 320, two (2) PMTs (namely, PMTs 310 and 312a) see the event most strongly, and two (2) others (namely, PMTs 312b and 312f) see it strongly as well. There is also a significantly large number of PMTs around these four (4) PMTs which can see the event, albeit relatively more weakly. If their outputs are used, the three (3) other PMTs (namely, PMTs 312c, 312d and 312e) can have a significant impact on the determined location of the event, and while they see the double point event relatively more weakly, it can still be significant enough to overcome the "percentage of total" threshold. However, in view of the relative weakness with which they see the scintillator light, the outputs of the three other PMTs 312c, 312d and 312e may be more largely based on individual gain variations, random noise, and other such factors which are not suitably reliable for positioning the event, rather than on the degree to which the scintillator light is seen. Near the triple point 322, the analogous problem occurs. It should be noted that the "percentage of total" threshold cannot simply be further increased to provide better spatial positioning, since such an increase tends to cause a larger "pincushion" effect near the high or center PMT 310 (i.e., undesirably, events progressively nearer the center PMT 310 are progressively less subject to the positioning influences of the outer six (6) PMTs 312a-312f).

Yet another approach for addressing the hexagonal artifact incorporates a compression scheme that reduces high PMT signals and amplifies low PMT signals. It can reduce the hexagon artifact, but only at the expense of position accuracy (i.e., it mis-positions events, which blurs out the true event position).

Thus, notwithstanding the foregoing approaches and/or techniques, it remained heretofore desirable to improve event localization. The present invention contemplates a new and improved gamma camera and technique therefore which overcomes the above-referenced problems and others.

In accordance with one aspect of the present invention, a method of locating an event with a gamma camera of an emission computed tomography (ECT) scanner is provided. The gamma camera includes a matrix of sensors situated to view the event. The sensors have respective outputs that are responsive to the event. The method includes: identifying a first sensor in the matrix that has in response to the event a highest output relative to the other sensors in the matrix; identifying a number of second sensors in the matrix that are closest neighbors to the first sensor; combining into a total output a number of outputs from the identified sensors, the number of outputs being at least one (1) and less than the number of all the identified sensors; and, determining a threshold value which is a percentage of the total output.

In accordance with another aspect of the present invention, a gamma camera is provided for locating a radiation event in an emission computed tomography (ECT) scanner. The gamma camera includes: a matrix of sensors situated to view the event, the sensors having respective outputs that are responsive to the event; means for identifying a first sensor in the matrix that has in response to the event a highest output relative to the other sensors in the matrix; means for identifying a number of second sensors in the matrix that are closest neighbors to the first sensor; means for combining into a total output a number of outputs from the identified sensors, the number of outputs being at least one (1) and less than the number of all the identified sensors; and, means for determining a threshold value which is a percentage of the total output.

In accordance with another aspect of the present invention, an emission computed tomography (ECT) scanner includes an examination region in which a subject being examined is situated, the subject containing a distribution of radionuclides. A detector has a matrix of sensors situated to view a radiation event emanating from the examination region, the sensors having respective outputs that are responsive to the event. A processor: (i) identifies a first sensor in the matrix that has in response to the event a highest output relative to the other sensors in the matrix; (ii) identifies a number of second sensors in the matrix that are closest neighbors to the first sensor; (iii) combines into a total output a number of outputs from the identified sensors, said number of outputs being at least one (1) and less than the number of all the identified sensors; and, (iv) determines a threshold value which is a percentage of the total output.

In accordance with another aspect of the present invention, a method of emission computed tomography (ECT) includes: approximating a location of a detected event with respect to a matrix of sensors that view the event, and determining if the approximated location of the detected event is substantially within effective boundaries of a sensor in the matrix. If it is determined that the approximated location of the detected event is substantially within effective boundaries of a sensor in the matrix, then a first number of sensors nearest the approximated location are sampled. Otherwise, if it is determined that the approximated location of the detected event is not substantially within effective boundaries of a sensor in the matrix, then a second number of sensors nearest the approximated location are sampled, the second number being less than the first number. A position for the detected event is generated from the sampled sensors.

One advantage of the present invention is the ability to improve image quality resulting from better spatial resolution and event positioning.

Another advantage of the present invention is the ability to reduce hexagon artifacts in images obtained from gamma cameras.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating preferred embodiments and are not to be construed as limiting the invention. The drawings are not to scale.

Figure 1:
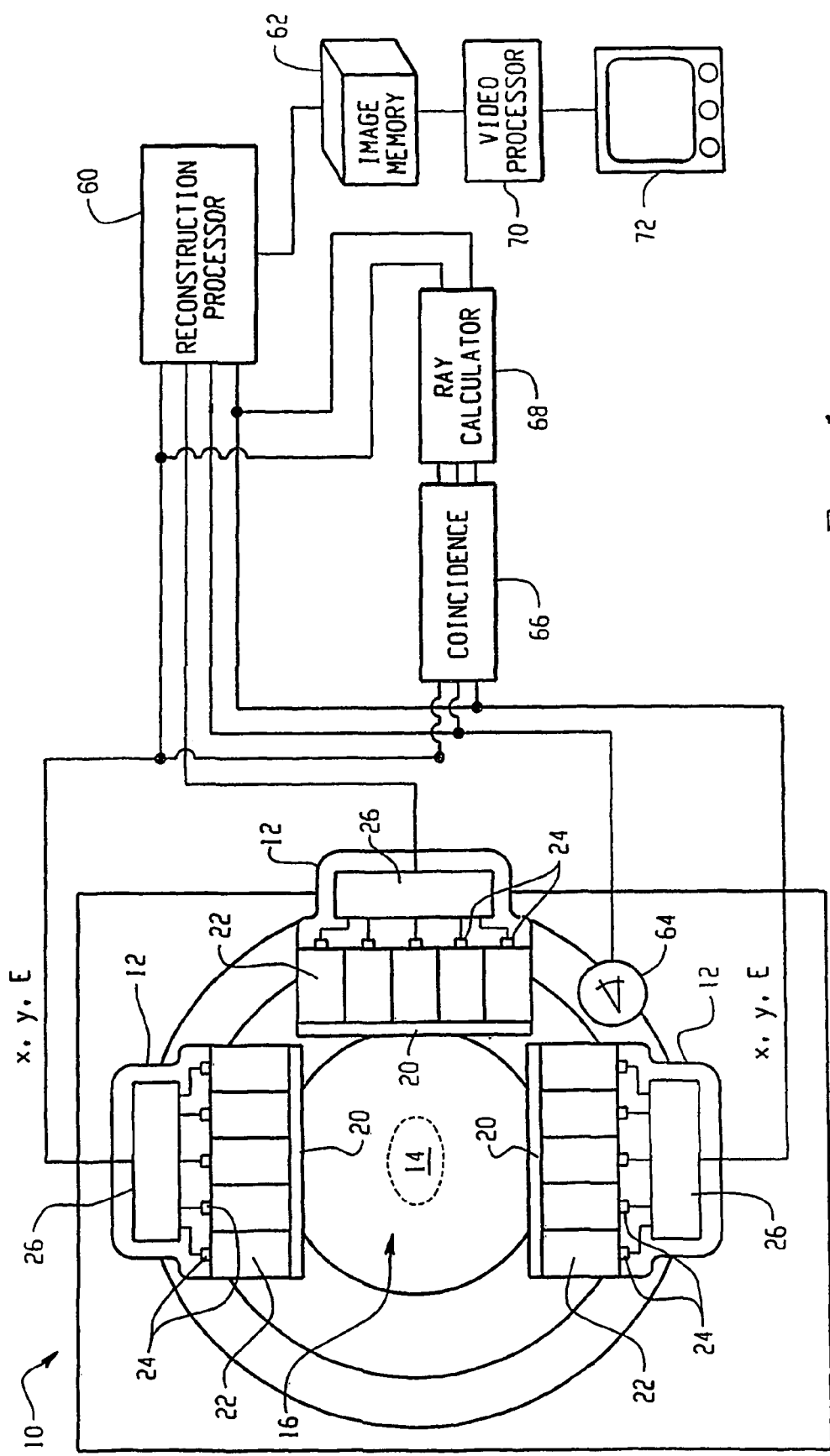
FIG. 1 is a diagrammatic illustration of an exemplary ECT scanner in accordance with aspects of the present invention.

With reference to FIG. 1, an ECT scanner 10 includes a plurality of detectors heads ("detectors") or gamma cameras 12 facing and mounted for movement around a subject 14 (preferably containing a radionuclide distribution) located in an examination region 16. Each of the detectors 12 includes a scintillator 20 that converts a radiation event (e.g., a ray of radiation from the radionuclide distribution that impinges on the scintillator 20) into a flash of light or scintillation. A matrix of sensors 22, e.g., 59 sensors, is situated to view or receive the light flashes from the scintillator 20. In the preferred embodiment, the matrix of sensors is a close hexagonal packed arrangement of PMTs. However, other sensors and packing arrangements are also contemplated.

Each of the sensors 22 generates a respective output signal, e.g., an analog electrical pulse, in response to a received light flash, the output signal being proportional to that of the received light flash. In the case of an analog signal output, each of the sensors 22 is optionally electrically connected to analog-to-digital (A/D) converters 24 that convert the respective analog outputs to digital signals. While "fully digital" cameras 12 are shown, "fully analog" or "hybrid analog/digital" cameras may also be suitably employed. As is discussed in more detail below, a processor 26 measures or otherwise determines the location and/or energy of respective scintillation events that occur. The location of an event on the scintillator 20 is resolved and/or determined in a two dimensional (2D) Cartesian coordinate system with nominally termed x and y coordinates. However, other coordinate systems are contemplated.

Figure 2:
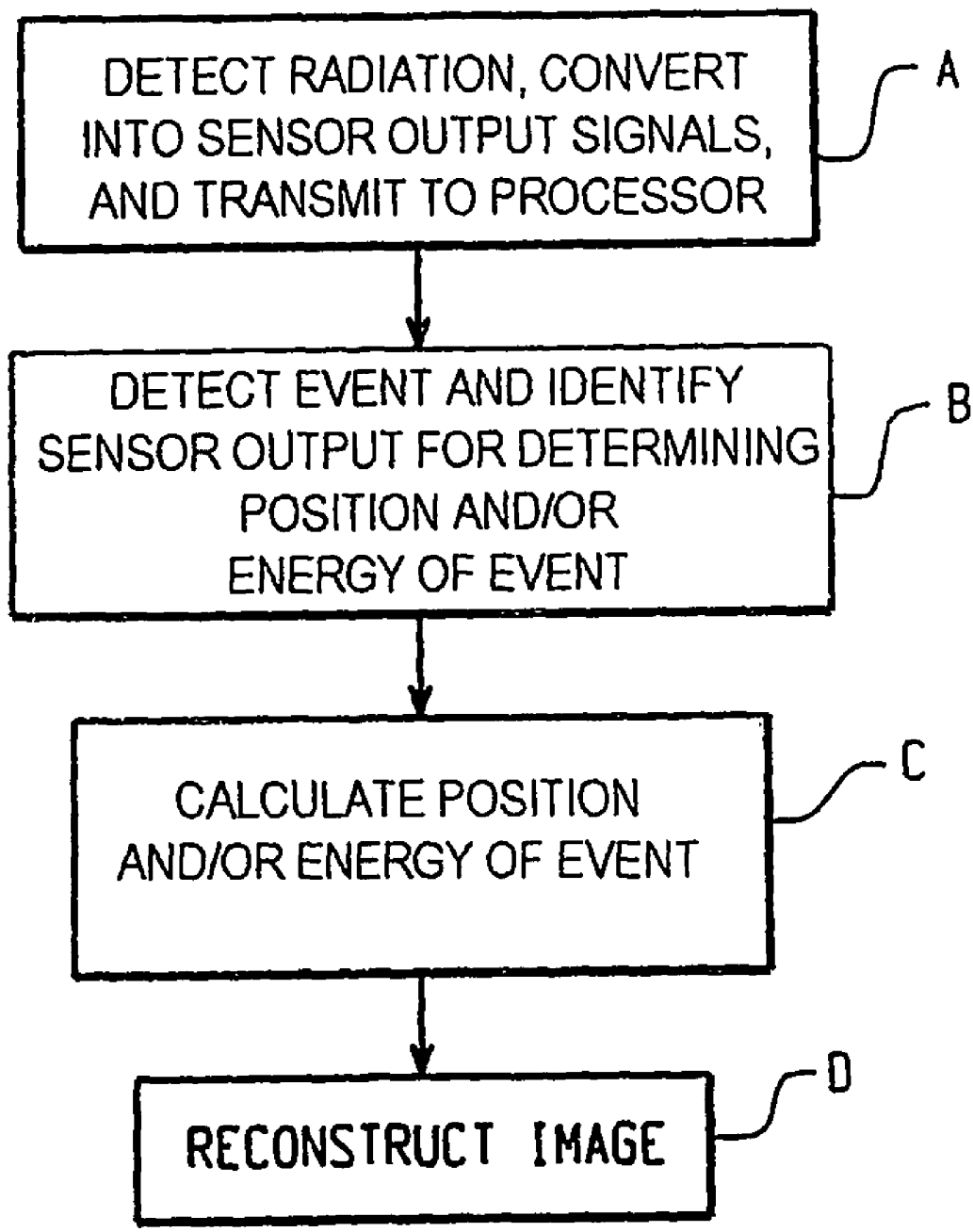
FIG. 2 is an overview flow chart showing an exemplary method in accordance with aspects of the present invention.

With reference to FIGS. 1 and 2, radiation is detected and converted into sensor output signal, which are transmitted to the processor 26 in a step A. Then, in a step B, the processor 26 detects that an event occurs and identifies and/or selects sensor outputs that will be used and/or sampled to determine the position and/or energy of the event. Optionally, at step B, in lieu of or in addition to selecting sensor outputs, the processor regulates the extent to which particular sensor outputs will contribute to the determination or calculation of an event's position and/or energy. In a step C, the processor 26 calculates or otherwise determines the position and/or energy of the event. Finally, in a step D, an image is reconstructed from the located events, the image being representative of the radionuclide distribution within the subject 14.

With reference to FIG. 24, each of the steps A and B includes a plurality of respective sub-steps, which are discussed below. For ease of explanation, each of the sub-steps is identified with a reference numeral specifying both the step (see FIG. 2) and the sub-step (see FIGS. 3 and 4).

Figure 3:
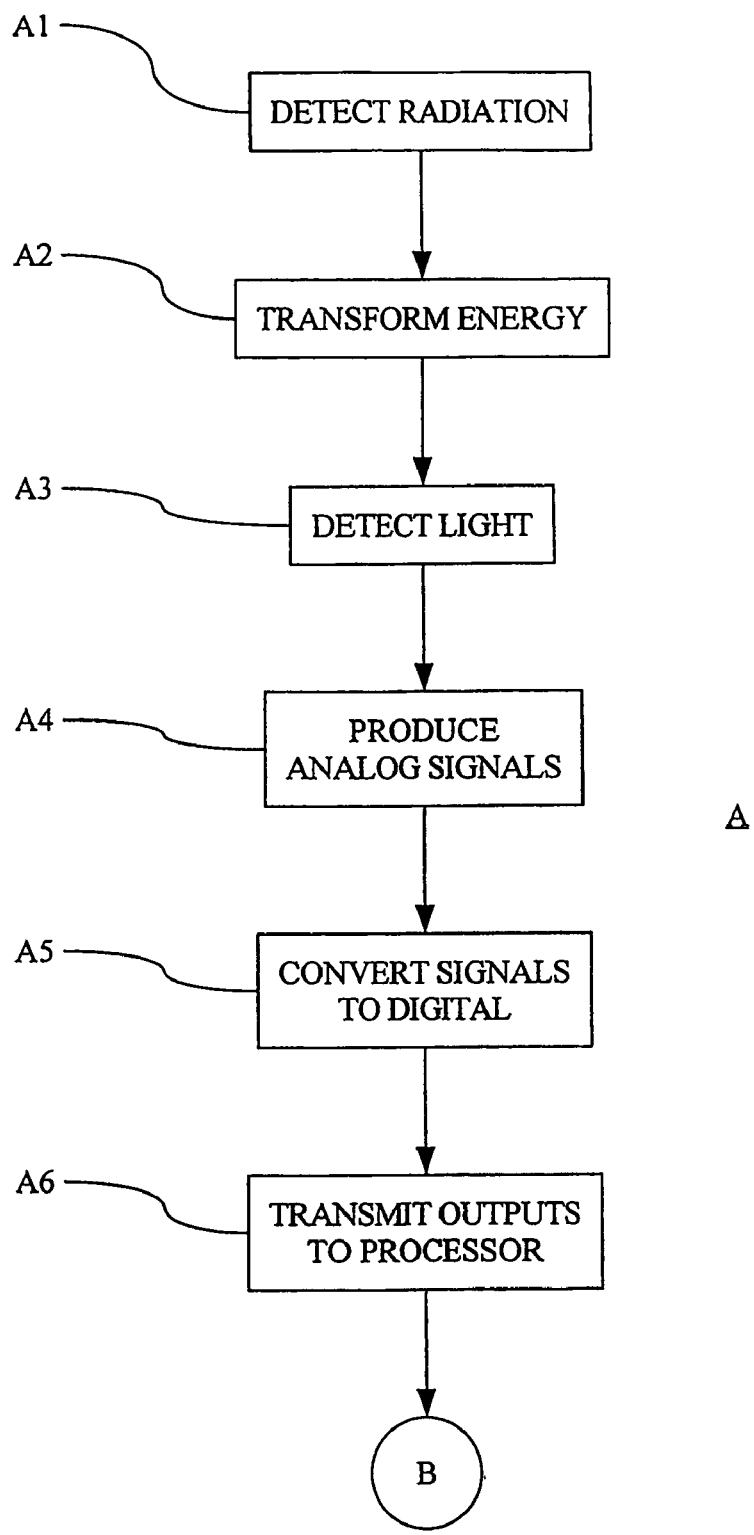
FIG. 3 is a flow chart showing exemplary sub-steps for carrying out a step shown in the flow chart of FIG. 2.
Figure 5:
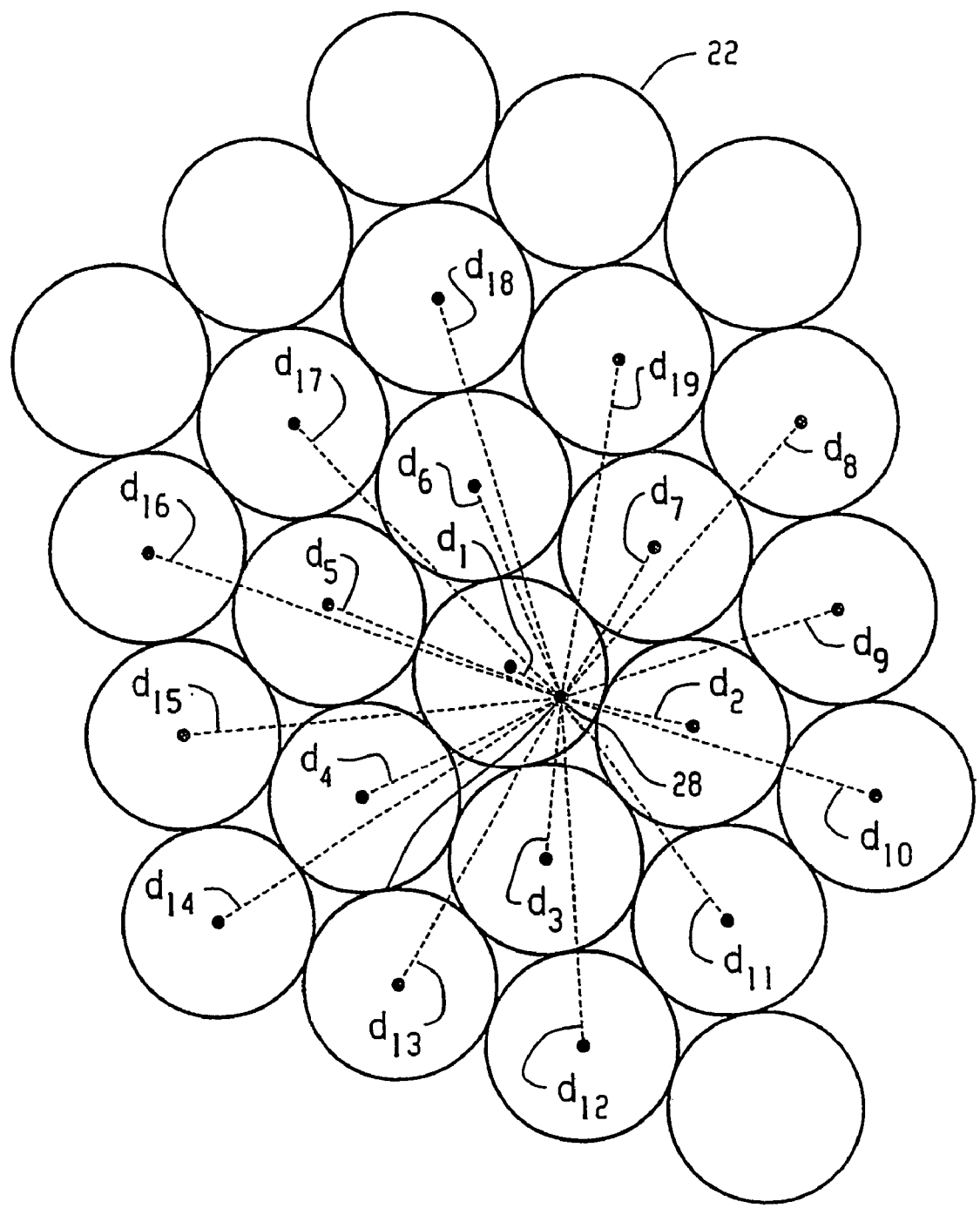
FIG. 5 is a diagrammatic illustration showing an exemplary spread of light from a scintillation event to a close packed hexagonal arrangement of sensors in accordance with aspects of the present invention.

With reference to FIGS. 1-3, each radiation event is detected within the matrix of sensors 22 in a sub-step A1. The radiation produces gamma quanta that arise in the disintegration of radioisotopes. The disintegration quanta strike the scintillator 20, which preferably includes doped sodium iodide (NaI), causing a scintillation. Light from the scintillation is distributed over a number of the sensors 22. As shown in FIG. 5, an exemplary scintillation, which is created by a radiation event, is centered at an arbitrary position 28. The amount of light from a particular scintillation that a given sensor 22 sees or receives tends to progressively diminish with the sensor's distance from the event (indicated by reference numerals d1-d19). It is to be understood that only a partial portion of the matrix of the sensors 22 is shown in FIG. 5.

The energy of the absorbed gamma quantum is converted, or transformed, into the flash of light at the position 28 by the scintillator 20 in a sub-step A2. The sensors 22 detect (receive) the scintillation light in a sub-step A3. Then, the sensors 22 produce their respective output signals in a sub-step A4. The relative the sensor output signals are proportional to the respective amounts of the scintillation light received by the sensors 22 in the sub-step A3. When employed, the A/D converters 24 convert analog output signals to respective digital output in a sub-step A5. The digital outputs are then transmitted to the processor 26 in a sub-step A6. For a given event, the output value of each sensor 22 is optionally determined by: integration of the sensor's output signal response to the event (i.e., finding the area or some portion thereof under a curve plotting amplitude or intensity vs. time for the output pulse of the sensor 22); the peak amplitude of the sensor's output signal response to the event; or, some other measure that is proportional or suitably related to the observed amount of light.

Figure 4:
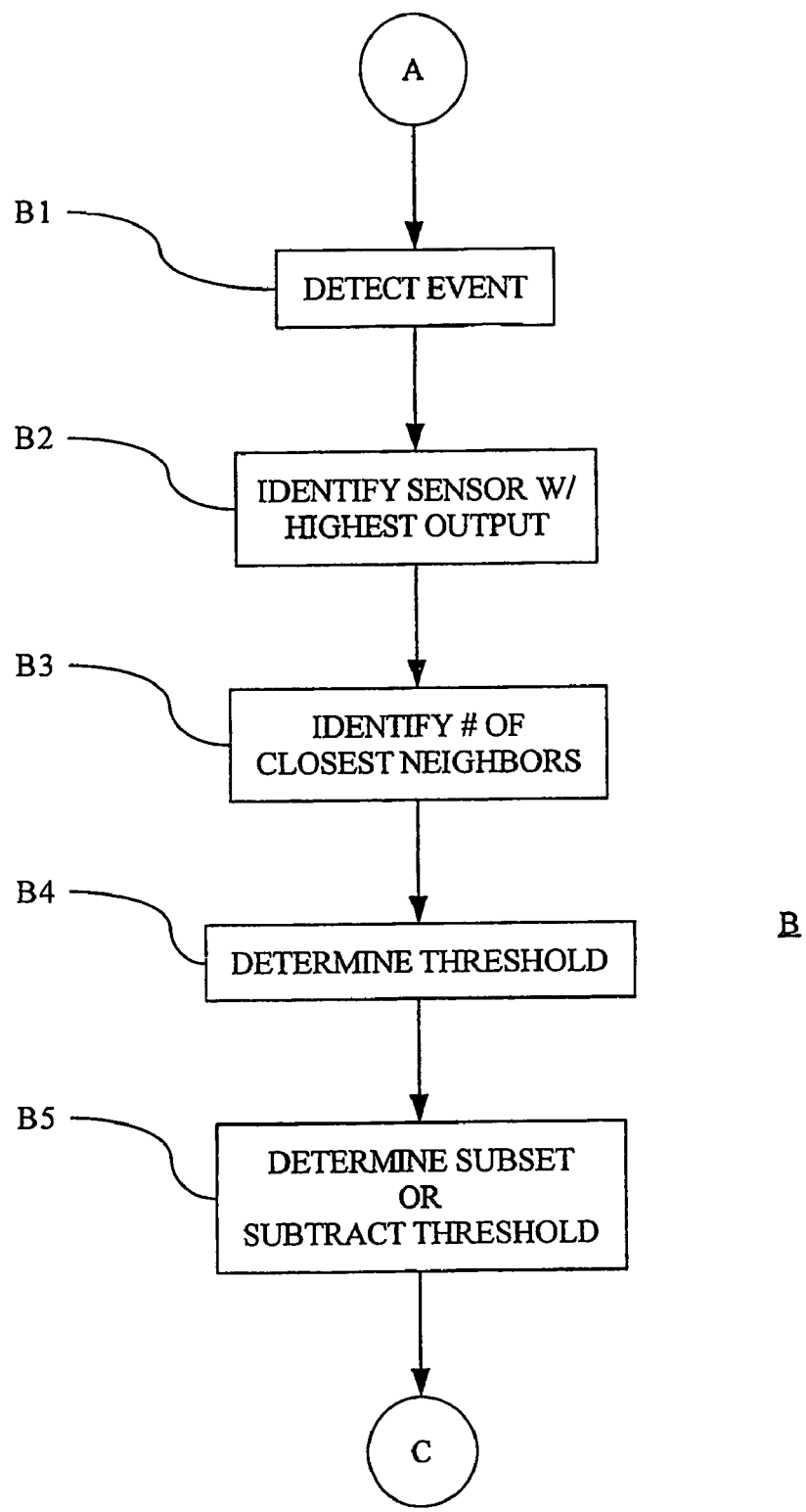
FIG. 4 is a flow chart showing exemplary sub-steps for carrying out a step shown in the flow chart of FIG. 2.

With reference now to FIGS. 1, 2 and 4, The processor 26 detects that an event occurs (starts) in a sub-step B1 by analyzing the output values for each of the sensors. In a preferred embodiment, the processor 26 triggers (detects) that an event occurs when a sensor output value surpasses a trigger amplitude.

In a sub-step B2, the sensor 22 having the highest output value relative to all the other sensors 22 is identified, and a number of closest neighboring sensors 22 thereto are also identified in sub-step B3. Suitably, in a close hexagonal packing matrix of sensors 22 (as shown in FIG. 5), the number closest neighboring sensors 22 identified is six (6), thereby defining a 7-PMT cluster, with the center sensor 22 being the identified one having the highest output value and the six (6) closest neighboring sensors 22 surrounding the same.

Figure 7:
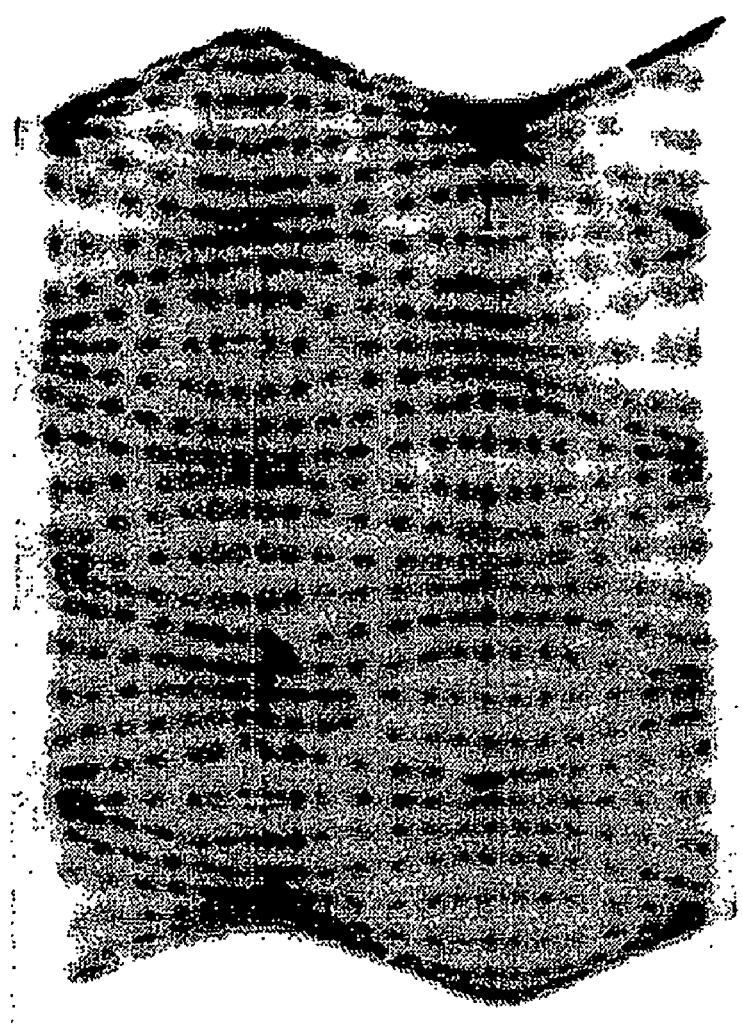
FIG. 7 is an illustration showing event data obtained in accordance with practicing aspects of the present invention.

In a sub-step B4, a threshold is dynamically determined for each detected event. The threshold is preferably not based on or a percentage of the total sum of output values from all the sensors 22 identified in sub-steps B2 and B3 (collectively referred to as the identified sensors). Rather, the threshold is based on or a percentage of an output value from one of the identified sensors, or alternately the threshold is based on or a percentage of the total sum of output values from multiple, but less than all, of the identified sensors (e.g., in a 7-PMT cluster, from 2 to 6 of the identified sensors). Preferably, in the case where a 7-PMT cluster is defined by the identified sensors, the threshold is calculated or otherwise determined as a percentage (e.g., 30%) of the output value from the identified sensor having the third highest output value. FIG. 7 illustrates exemplary event data obtained in accordance with such an embodiment. However, other percentages are also contemplated, and it is contemplated to also base the percentage on the output value of an identified sensor having a relative output value ranked other than the third highest. Similarly, it is contemplated to base the percentage on the summed output values of multiple, but less than all, of the identified sensors having relative output values of various ranks, e.g., ranked second and third highest.

In a sub-step B5, it is determined which of the identified sensors have output values that meet or exceed the threshold determined in sub-step B4. Such sensors are referred to as the identified subset of sensors. Used in this regard, the term "subset" encompasses a set which has as its members all of the identified sensors. In step C then, the position of a particular event is determined using only output values obtained from the identified subset of sensors determined in sub-step B5, i.e., without factoring in output values from sensors that are not members of the identified subset. The position is preferably calculated as the centroid of the output values obtained from the identified subset of sensors, e.g., using an Anger sum that omits output values from sensors that are not members of the identified subset.

Alternately, rather than omitting from the position determination those output values from identified sensors not meeting or exceeding the determined threshold, the output values from all the identified sensors may be reduced by the determined threshold amount thereby effectively eliminating any contributions from identified sensors having output values below the threshold in a subsequent position determination that uses the so modified output values from all the identified sensors. More specifically, in sub-step B5, the determined threshold value from sub-step B4 is subtracted from the output values of all the identified sensors from sub-steps B2 and B3, with negative results being given a zero (0) value. Then, at step C, the position of a particular event is determined using the resulting output values (as reduced in sub-step B5) from all the identified sensors.

Figure 6:
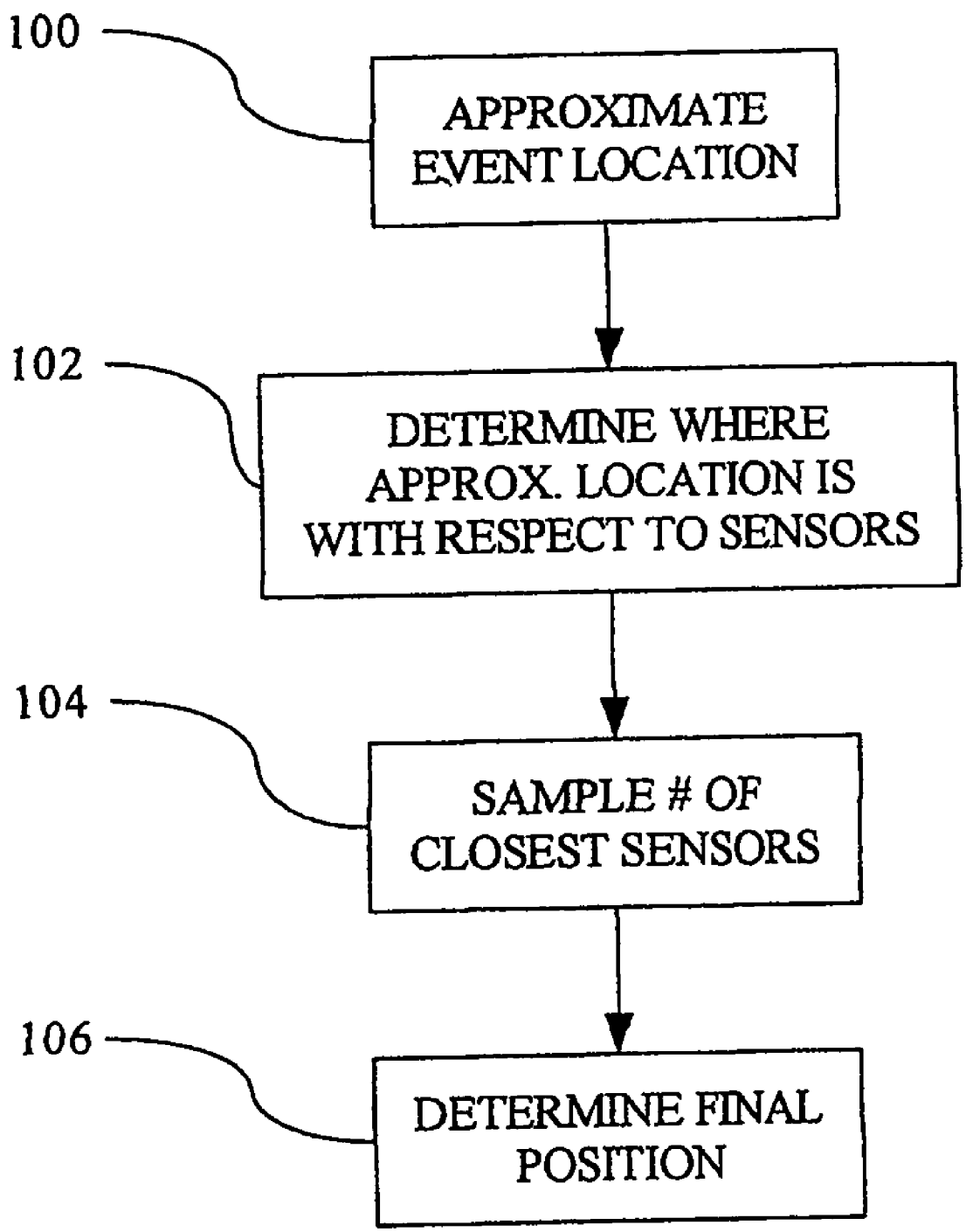
FIG. 6 is a flow chart showing an exemplary method in accordance with aspects of the present invention.
Figure 8:
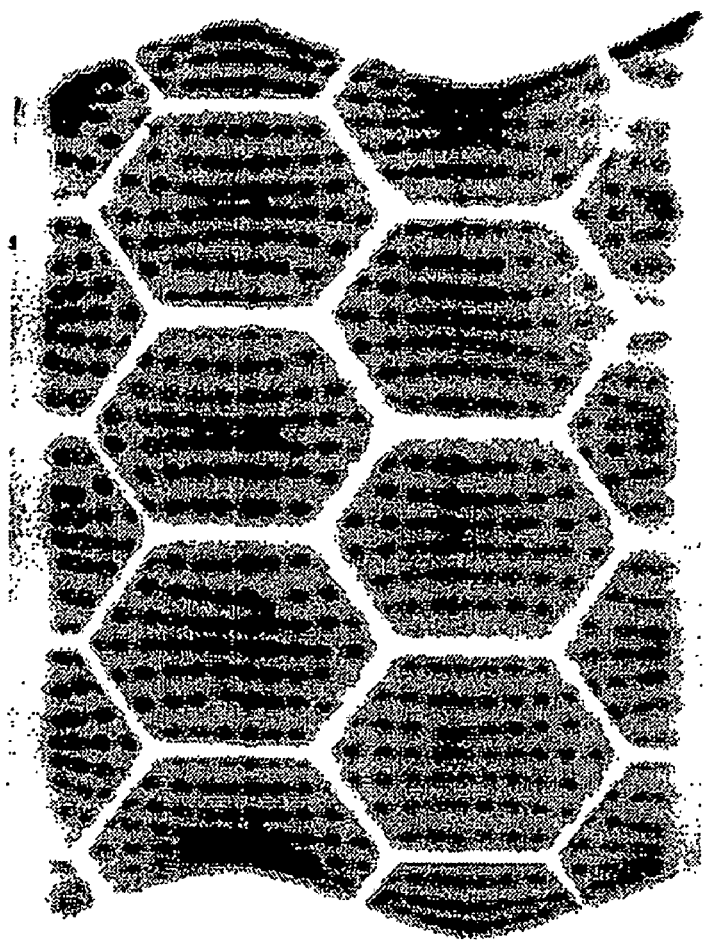
FIG. 8 is an illustration showing event data obtained in accordance with practicing a prior art approach.
Figure 9:
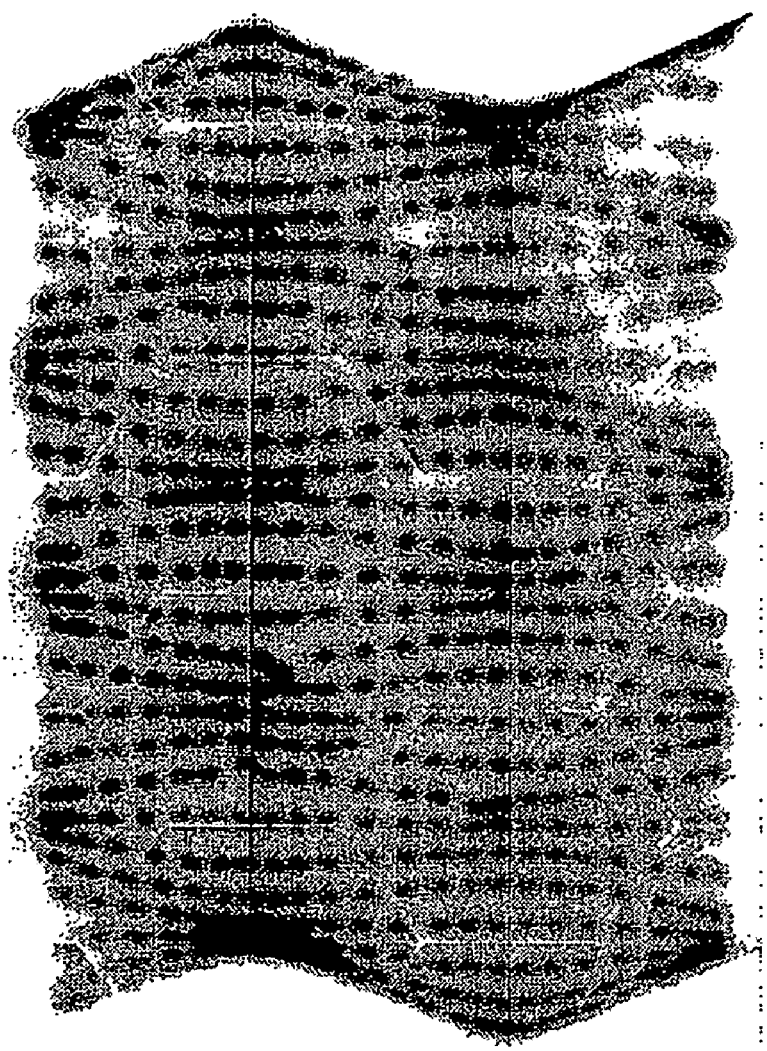
FIG. 9 is an illustration showing event data obtained in accordance with practicing a prior art approach.

As can be readily appreciated by contrasting FIG. 7 with FIGS. 8 and 9, the result is a relative reduction in mispositioning events as evidenced by the significant (in fact, the nearly complete) elimination of the hexagonal artifact. Considering, e.g., the case where the identified sensors define a 7-PMT cluster in a close hexagonal packed matrix of sensors, and the threshold is set to be approximately 30% of the output value obtained from the PMT with the third highest ranked output value in accordance with the technique proposed herein. When an event is near the center PMT, all outer six (6) PMT outputs will likely be above the threshold due to the PMTs proximity to the event, and the center PMT output will surely be above the threshold as it has the highest ranked output which is by definition greater than 30% of the output value obtained from the PMT with the third highest ranked output. Accordingly, to advantage in event positioning, the outputs of all seven (7) PMTs will be properly included in the position determination or Anger sum. However, for events occurring nearer the boundaries of the center PMT or between PMTs, less than all the output values will contribute to the positioning determination. For example, in the vicinity of a triple point, only the three (3) PMTs nearest the event are likely to have outputs above the threshold due to the PMTs' respective distances therefrom. Again, to advantage in event positioning, the outputs from the more remote PMTs will properly not contribute to the position determination or not be included in the Anger sum. In this manner, the above-described problem associated with events occurring in these regions (i.e., at or near the triple point and similarly the double point) is resolved. Along these lines, in another suitable sensor output selection method (as shown in FIG. 6), an approximation of an event location is determined at a step 100. Then, it is determined at a decision step 102, if the approximate location is at or near a boundary of a sensor 22 or is between sensors 22. If the approximate location is soundly within the boundaries of a sensor 22, then at a step 104 a first number of sensors nearest the approximate location are sampled to generate the final position determination in a step 106, e.g., employing an Anger sum. Otherwise, if the approximate location is determined in step 102 to be at or near a boundary of a sensor or is between sensors, then at step 104 a second number (less than the first number) of sensors nearest the approximate location are sampled to generate the final position determination in step 106.

The scanner 10 illustrated in FIG. 1 is selectively operable as desired in either a SPECT mode or a PET mode. In the SPECT mode, the cameras 12 have collimators attached thereto which limit acceptance of radiation to particular directions, i.e., along known rays. Thus, the determined location on the scintillator 20 at which radiation is detected and the angular position of the camera 12 define the ray along which each radiation event occurred. These ray trajectories and camera angular positions (e.g., obtained from an angular position resolver 64) are conveyed to a reconstruction processor 60 which backprojects or otherwise reconstructs the rays into a volumetric image representation in an image memory 62.

In the PET mode, the collimators are removed. Thus, the location of a single scintillation event does not define a ray. However, the radionuclides used in PET scanning undergo an annihilation event in which two photons of radiation are emitted simultaneously in diametrically opposed directions, i.e., 180 degrees apart. A coincidence detector 66 detects when scintillations on two cameras 12 occur simultaneously. The locations of the two simultaneous scintillations define the end points of a ray through the annihilation event. A ray or trajectory calculator 68 calculates the corresponding ray through the subject 14 from each pair of simultaneously received scintillation events. The ray trajectories form the ray calculator 68 are conveyed to the reconstruction processor 60 for reconstruction into a volumetric image representation.

In both SPECT and PET modes, a video processor 70 processes and/or formats the image representation data for display on a monitor 72.

Figure 10:
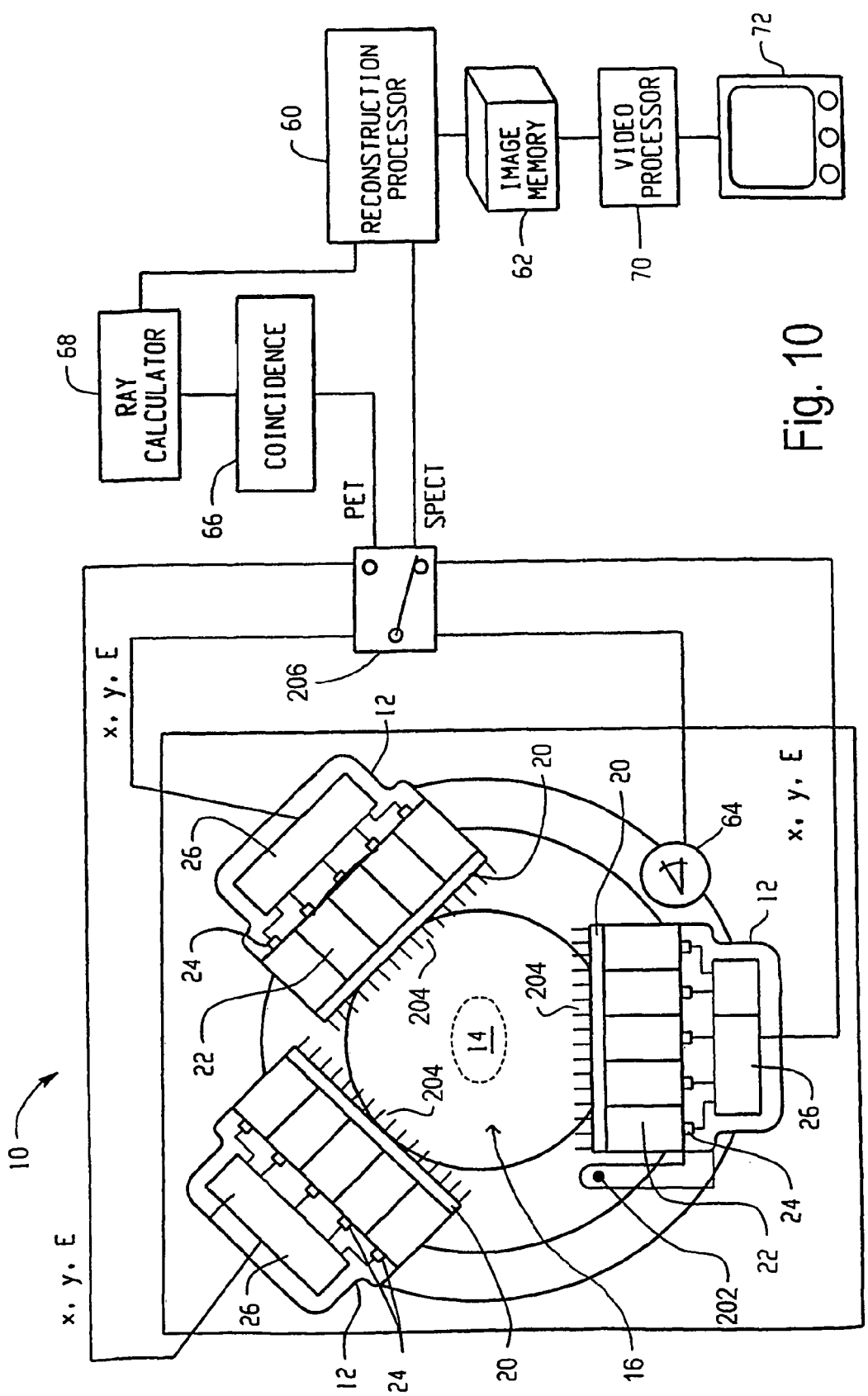
FIG. 10 is a diagrammatic illustration of another exemplary ECT scanner in accordance with aspects of the present invention.
Figure 11:
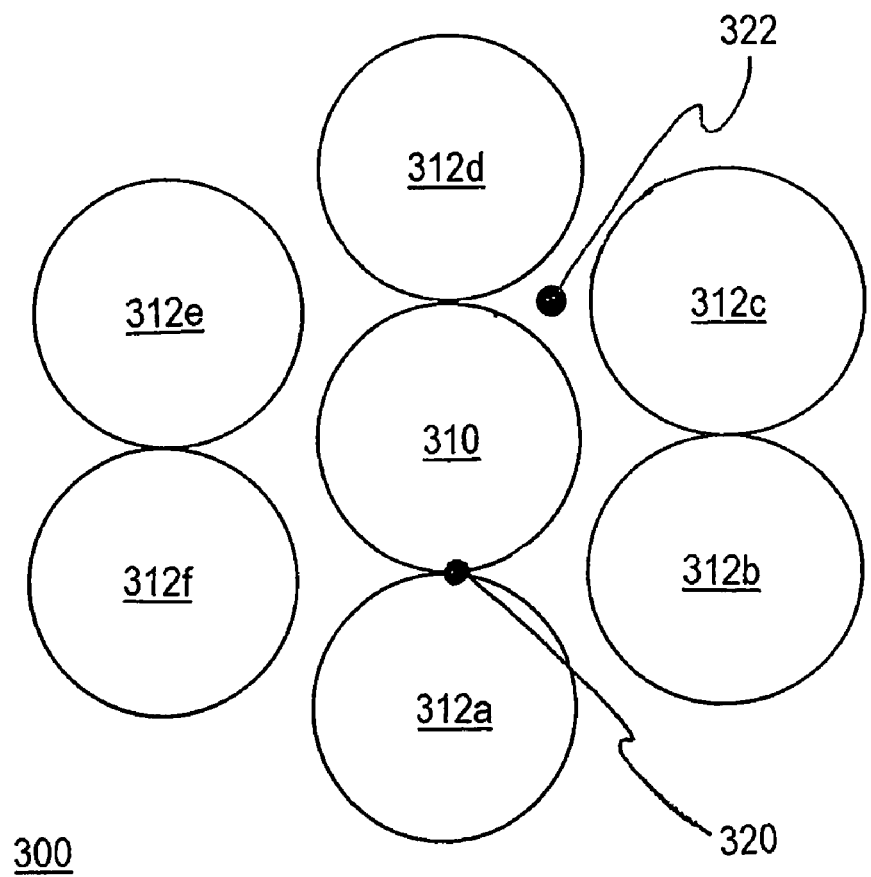
FIG. 11 is a diagrammatic illustration showing exemplary locations of double and triple points in a close packed hexagonal 7-PMT cluster.

With reference to FIG. 10, a scanner in accordance with another embodiment of the present invention is illustrated. For ease of understanding this embodiment, like components are designated by like reference numerals and previously unreferenced components are designated by new numerals. The scanner 10 includes three (3) detectors or cameras 12 mounted for movement around the subject 14 situated in an examination region 16, the subject being injected with a radionuclide that emits emission radiation. Each of the detectors 12 includes a scintillator 20 for converting radiation events from the injected radionuclide into a flash of light energy or scintillation. Optionally, a radiation source 202 produces a fan of transmission radiation of a different energy than the emission radiation. Collimators 204 on the detectors 20 limit and define the paths or rays along which each detector 20 accepts emission and transmission radiation. The location of a resulting scintillation and the position of the receiving detector 20 uniquely determine the ray. That is to say, the processor 26 determines the energy and the location of each scintillation on the face of the detectors 20, hence the ray along which the radiation originated. Once the positions and energies are determined at which scintillations occurred and from the respective positions of the detectors 20, the reconstruction processor 60 reconstructs an image representation from the emission data, which is distinguished via the determined energy associated with the data. When the radiation source 202 is used, transmission data (similarly identified via the energy associated with the data) is used to correct the emission data for an improved image, e.g., by generating an attenuation map or the like of the subject. 14. The image representation is stored in the image memory 62, and accessing the same, the video processor 70 processes the image representation data for display on the monitor 72. Again, the scanner 10 can be used without collimators 204 in a PET mode. A switch or other suitable control 206 is optionally provided for mode selection. It is to be appreciated that while shown arranged on one of the cameras 20, the radiation source 202 is optionally disposed elsewhere.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiments, the invention is now claimed to be:

1. A method of generating a diagnostic image with a gamma camera of an emission computed tomography (ECT) scanner, said gamma camera including a matrix of sensors situated to view the event, said sensors having respective outputs that are responsive to the event, said method comprising:
    (a) identifying a first sensor in the matrix that has in response to the event a highest output relative to the other sensors in the matrix;
    (b) identifying a sensor in the matrix that has, in response to the event, a third highest output relative to other sensors in the matrix;
    (c) based on the first and third highest outputs, determining a number of second sensors in the matrix that are closest neighbors to the first sensor and identifying such second sensors;
    (d) sampling outputs from the identified first and second sensors, said number of outputs being at least three and less than the number of all the identified sensors;
    (e) determining an event location with the sampled outputs;
    (f) repeating steps (a)-(e) to determine a plurality of event locations;
    (g) forming the plurality of event locations into a human viewable image.

2. The method of claim 1, wherein determining and identifying the second sensors includes:
    determining a threshold based on the third highest output;
    using outputs greater than or equal to the threshold value to determine the event location.

3. The method of claim 2, further comprising:
    sampling outputs in response to the event from all the identified sensors;
    reducing respective sampled outputs by the threshold value; and,
    determining a location of the event with the reduced sampled outputs.

4. The method of claim 1, wherein the number of identified first and second sensors is one of three, four, and seven.

5. The method of claim 1, wherein the sensors are photomultiplier tubes (PMTs).

6. A computer readable medium coded with a program for controlling a computer to perform the method of claim 1.

7. A gamma camera for locating a radiation event in an emission computed tomography (ECT) scanner, said gamma camera comprising:
    a matrix of sensors situated to view the event, said sensors having respective outputs that are responsive to the event;
    means for identifying a first sensor in the matrix that has in response to the event a highest output relative to the other sensors in the matrix and a second sensor that has a third highest output;
    means for determining a subset of the sensors in the matrix that are closest neighbors to the first sensor and identifying such second sensors based on the first and third highest outputs;
    means for sampling outputs from the identified sensors; and,
    means for determining a location of the event.

8. The gamma camera of claim 7, further comprising:
    means for determining a threshold using the third highest output;
    means for determining which of the identified sensors have in response to the event an output that is greater than or equal to the threshold value to identify the subset of closest neighbor sensors.

9. The gamma camera of claim 7, further comprising:
    means for sampling outputs in response to the event from all the identified sensors;
    means for reducing respective sampled outputs by a threshold value; and,
    the means for determining the location of the event using the reduced sampled outputs.

10. The gamma camera of claim 7, further comprising:
    a scintillator that converts radiation events incident thereon into flashes of light that are viewed by the matrix of sensors.

11. The gamma camera of claim 10, wherein the sensors are photomultiplier tubes (PMTs).

12. The gamma camera of claim 11, wherein the matrix is arranged in a close packed hexagonal pattern.

13. The gamma camera of claim 12, wherein the identified sensors are selected using the third highest output to define one of a 3-PMT cluster a 4-PMT cluster and a 7-PMT cluster.

14. An emission computed tomography (ECT) scanner comprising:
    an examination region in which a subject being examined is situated, said subject containing a distribution of radionuclides;

a detector having a matrix of sensors situated to view a radiation event emanating from the examination region, said sensors having respective outputs that are responsive to the event; and, a processor that:
(i) identifies a first sensor in the matrix that has in response to the event a highest output relative to the other sensors in the matrix;
(ii) identifies a second sensor in the matrix that has a third highest output relative to the other sensors in the matrix;
(iii) determines a subset of the sensors in the matrix that are closest neighbors to the first sensor and identifies such subset of the sensors based on the third highest output, the subset including the sensor with the third highest output;
(iv) samples outputs from the first sensor and the subset of closest neighbor sensors; and,
(v) determines a location of the event from the sampled outputs.

15. The emission computed tomography (ECT) scanner of claim 14, wherein the processor further:
(vi) determines a threshold value using the third highest output;
(vii) reduces respective sampled outputs by the threshold value; and,
(viii) determines the location of the event with the reduced sampled outputs.

16. A method of emission computed tomography (ECT), comprising:
(a) approximating a location of a detected event with respect to a matrix of sensors that view the event;
(b) determining if the approximated location of the detected event is one of: substantially within effective boundaries of a sensor in the matrix, substantially at a double point between two nearest sensors, and substantially at a triple point between three nearest sensors;
(c) when it is determined that the approximated location of the detected event is substantially within effective boundaries of a sensor in the matrix, then seven sensors nearest the approximated location are sampled;
(d) when it is determined that the approximated location of the detected event is substantially at a double point, then four sensors nearest the approximated location are sampled; and,
(e) when it is determined that the approximated location of the detected event is substantially at a triple point, then the three nearest sensors are sampled;
(f) generating a position for the detected event from the sampled sensors;
(g) repeating steps (a)-(f) for a plurality of events;
(h) generating an image based on the positions generated in step (f).

17. A method of forming an image with a gamma camera, the method comprising:
identifying a first sensor of a hexagonal array of sensors that has the highest response to an event;
identifying another sensor that has a third highest response to the event;
determining a threshold level is determined based on the third highest response to the event;
using the threshold level to identify a number of second sensors surrounding the first sensor;
using responses of the first and second sensors to identify a location of the event;
reconstructing an image from a plurality of events, whereby the image is substantially free of hexagonal artifacts.

18. A computer readable medium coded with a program for controlling a computer to perform the method of claim 17.

19. A method of forming an image comprising:
providing a plurality of sensors;
identifying a first sensor that has the highest response to an event;
determining a number of second sensors proximate to the first sensor and identifying such second sensors, wherein the number of second sensors is dynamically adjusted based on a threshold level established by the sensor having the third highest response in response to the event; and
using the data from the identified sensors to reconstruct an image.

* * * * *